US00PP36251P2

(12) United States Plant Patent
van der Velden

(10) Patent No.: US PP36,251 P2
(45) Date of Patent: Nov. 12, 2024

(54) ***VRIESEA* PLANT NAMED 'Multred'**

(50) Latin Name: ***Vriesea* hybrid**
Varietal Denomination: Multred

(71) Applicant: Josephus van der Velden, Sint-Oedenrode (NL)

(72) Inventor: Josephus van der Velden, Sint-Oedenrode (NL)

(73) Assignee: HANDELSKWEKERIJ VAN DER VELDEN BV, Sint-Oedenrode (NL)

( * ) Notice: Subject to any disclaimer, the term of this patent is extended or adjusted under 35 U.S.C. 154(b) by 0 days.

(21) Appl. No.: 18/585,437

(22) Filed: Feb. 23, 2024

(51) Int. Cl.
*A01H 5/02* (2018.01)
*A01H 6/22* (2018.01)

(52) U.S. Cl.
USPC ..... Plt./370
CPC ..... *A01H 6/228* (2018.05)

(58) Field of Classification Search
USPC ..... Plt./370
CPC ..... A01H 6/228; A01H 5/02
See application file for complete search history.

*Primary Examiner* — Keith O. Robinson
(74) *Attorney, Agent, or Firm* — Penny J. Aguirre

(57) ABSTRACT

A new cultivar of *Vriesea* plant named 'Multred' that is characterized by its broad and flattened shaped inflorescences and its inflorescences with conduplicate bracts that are vibrant red in color.

3 Drawing Sheets

Botanical classification: *Vriesea* hybrid.
Cultivar designation: 'Multred'.

CROSS REFERENCE TO A RELATED APPLICATION

This application is related to a European plant breeders' rights application filed on Sep. 26, 2022, application No. 2022/1906. The Applicant received the information for the Plant breeders' rights application directly from the Inventor.

BACKGROUND OF THE INVENTION

The present invention relates to a new and distinct cultivar of *Vriesea* plant of hybrid origin, botanically known as *Vriesea* 'Multred' and will be referred to hereafter by its cultivar name, 'Multred'. 'Multred' is a new tropical bromeliad plant used as a landscape and container plant.

The new cultivar of *Vriesea* arose from a breeding program conducted by the Inventor in Sint-Oedenrode, The Netherlands with the goal of developing new *Vriesea* cultivars with clump-like inflorescences. The Inventor made a cross in June of 2015 between *Vriesea* 'Astrid' (not patented) as the female parent and unpatented plant of *Vriesea bleheri* as the male parent. The Inventor selected 'Multred' as a single unique plant amongst the seedlings that resulted from the above cross in September of 2019.

Asexual propagation of the new cultivar was first accomplished by cuttings in Sint-Oedenrode, The Netherlands in September 2019 by the Inventor. Asexual propagation by cuttings and tissue culture using meristematic tissue has determined that the characteristics of this cultivar are stable and are reproduced true to type in successive generations.

SUMMARY OF THE INVENTION

The following traits have been repeatedly observed and represent the characteristics of 'Multred'. These attributes in combination distinguish 'Multred' as a new and distinct cultivar of *Vriesea*.

1. 'Multred' exhibits broad and flattened shaped inflorescences.
2. 'Multred' exhibits inflorescences with conduplicate bracts that are vibrant red in color.

The female parent of 'Multred' differs from 'Multred' in having conduplicate bracts that are duller red in color and inflorescences that are less broad. The male parent of 'Multred' differs from 'Multred' in having inflorescence conduplicate bracts that are yellow in color and upper leaf surfaces that are duller green in color. 'Multred' can be most closely compared to *Vriesea* cultivars 'Shannon' (not patented) and 'Valetta' (not patented). 'Shannon' is similar to 'Multred' in being floriferous and in having a similar plant shape. 'Shannon' differs from 'Multred' in having inflorescences that are rounded (versus flattened) in cross-section and conduplicate bracts that are yellow in color. 'Valetta' is similar to 'Multred' in overall inflorescence shape. 'Valetta' differs from 'Multred' in having smaller inflorescences that are rounded (versus flattened) in cross-section and conduplicate bracts that are yellow-red in color.

BRIEF DESCRIPTION OF THE DRAWINGS

The accompanying color photographs illustrate the overall appearance and distinct characteristics of the new *Vriesea*. The photographs were taken of an 18-month-old plant as grown in a conventional greenhouse in a 11-cm container in Waddinxveen, The Netherlands.

The photograph in FIG. 1 provides a side view of 'Multred' in bloom.

Figure 1:
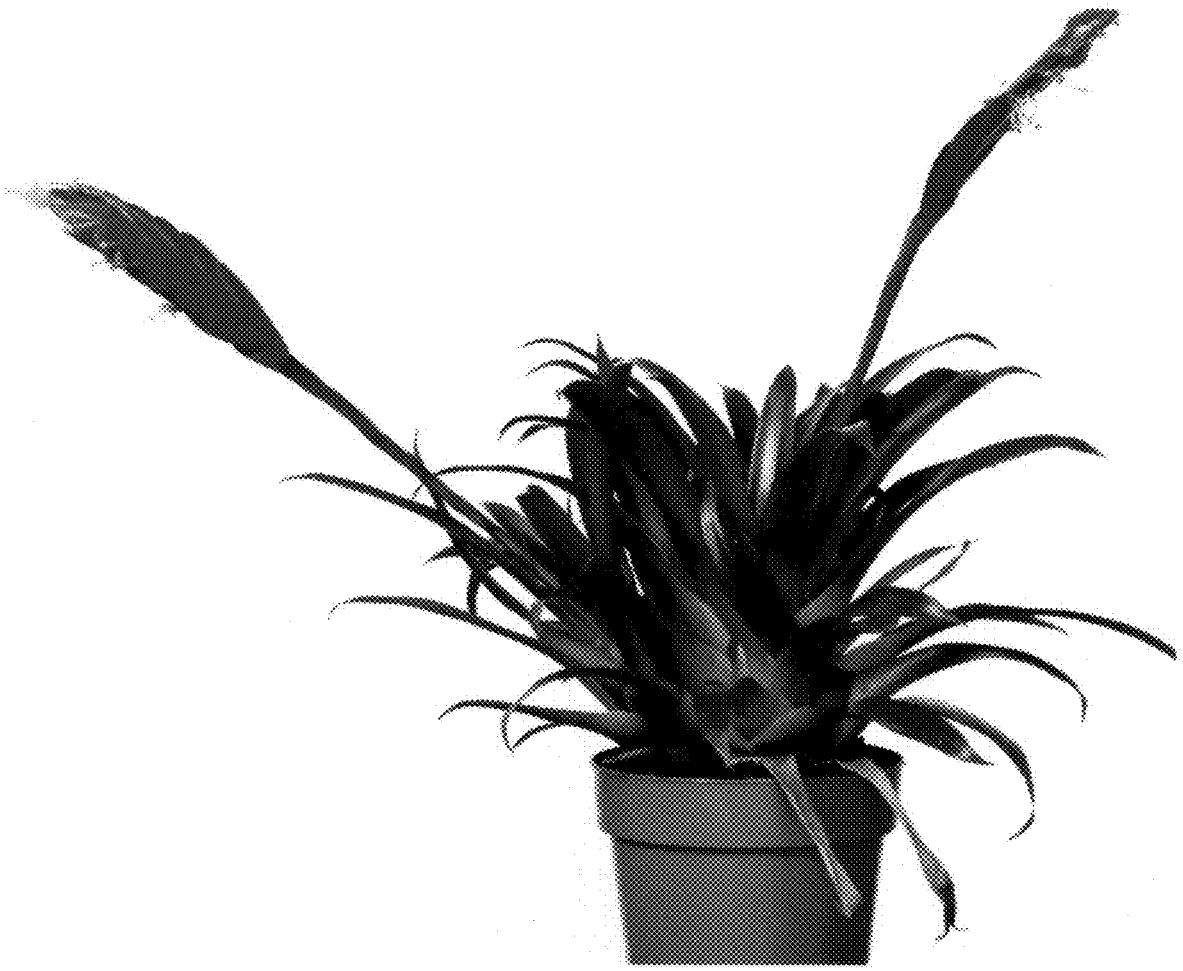
Figure 2:
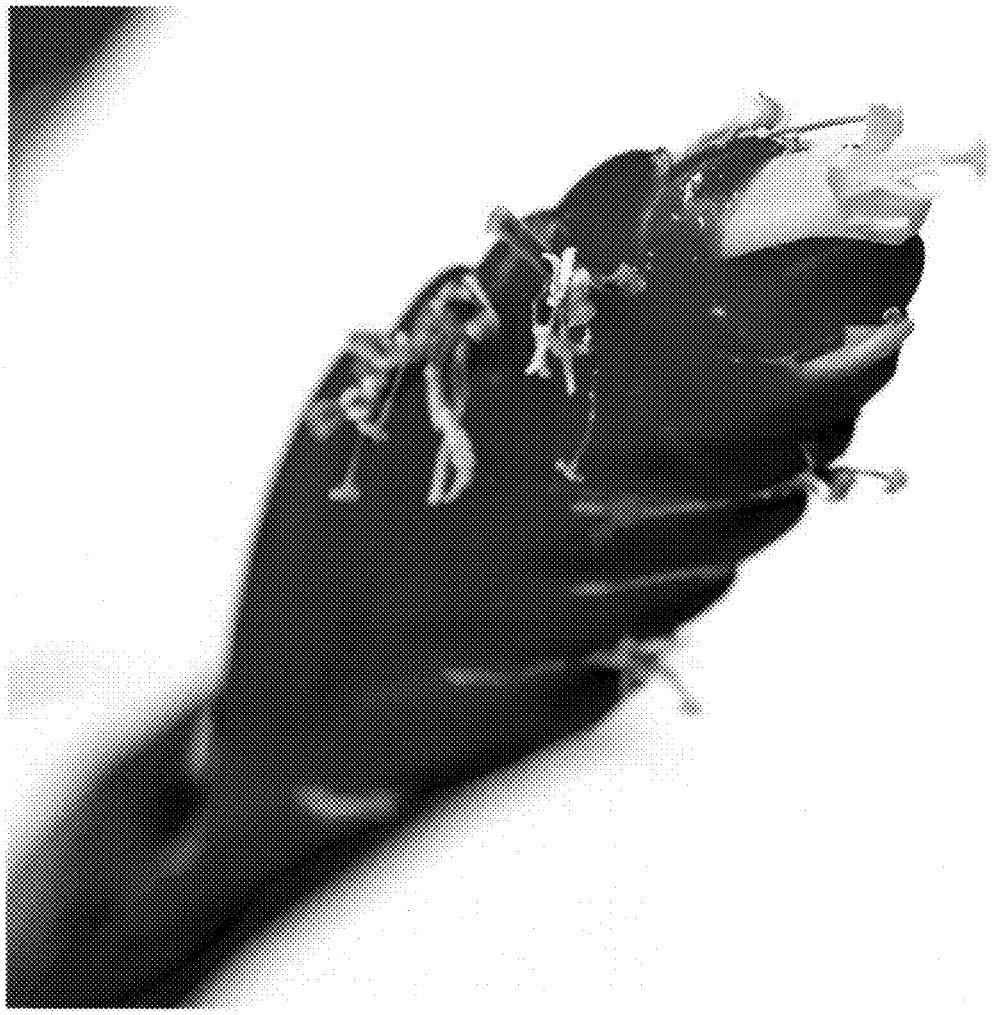

The photograph in FIG. 2 provides a close-up view of an inflorescence of 'Multred'.

Figure 3:
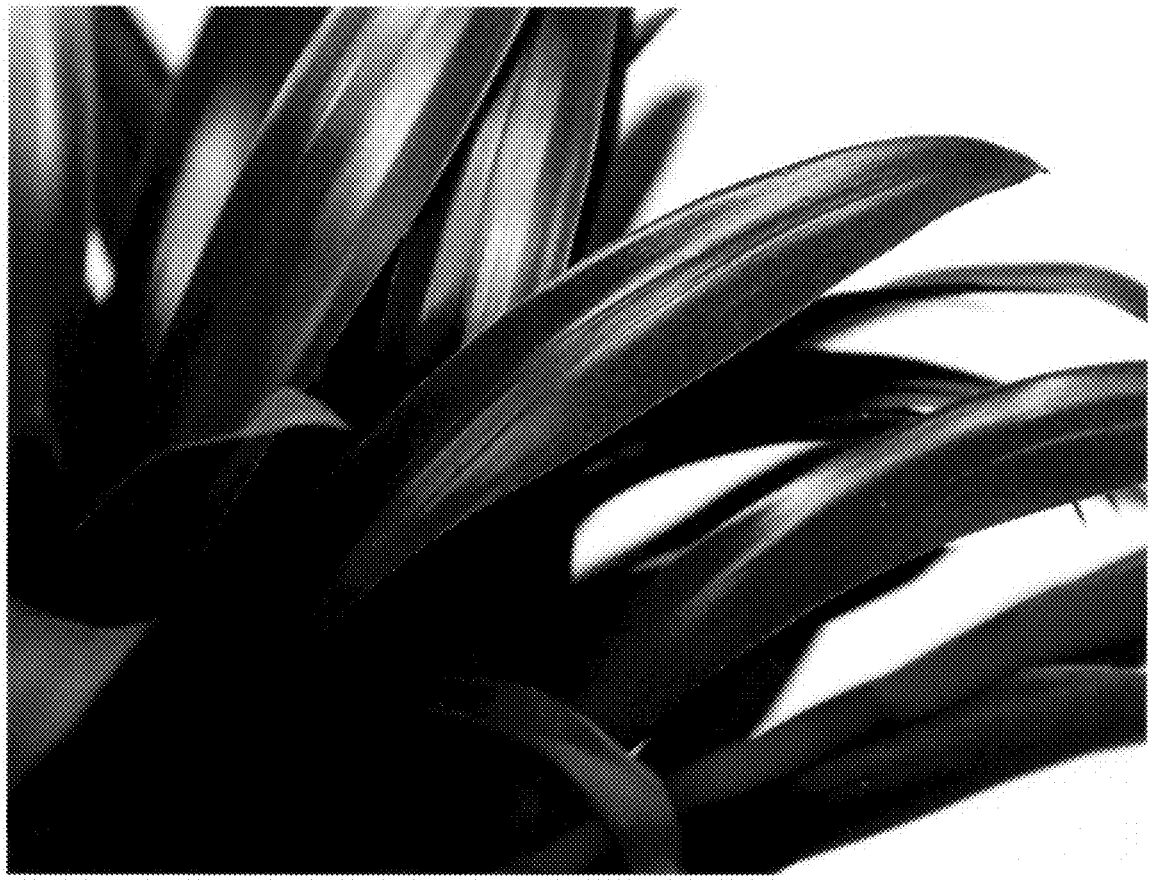

The photograph in FIG. 3 provides a close-up view of the foliage of 'Multred'.

The colors in the photographs are as close as possible with the digital photography and printing techniques utilized and the color codes in the detailed botanical description accurately describe the new *Vriesea*.

DETAILED BOTANICAL DESCRIPTION OF THE PLANT

The following is a detailed description of 18-month-old plants of the new cultivar as grown in a conventional greenhouse in a 11-cm container in Waddinxveen, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General characteristics:

*Blooming period*.—No specific blooming period, flowers may be produced throughout the year.

*Plant type*.—Tropical perennial.

*Plant habit*.—Flattened globular, monopodial with arching leaves.

*Height and spread*.—Average of 17 cm in height (soil level to top of foliar plane), 29.8 cm in height (soil level to top of floral plane), and 36.5 cm in width as an 18-month- old plant grown in a container, fully mature plants reach an average of 40 cm in height and spread.

*Hardiness*.—At least in U.S.D.A. Zones 10 to 12.

*Diseases and pests*.—No susceptibility or resistance to diseases or pests has been observed.

*Root description*.—Fleshy.

*Propagation type*.—Tissue culture and stem cuttings.

*Root development*.—In tissue culture; an average of 10 weeks for root initiation, 26 weeks to produce a fully rooted cutting.

*Growth rate*.—Moderate.

*Branching*.—Rosette.

Foliage description:

*Leaf shape*.—Ligulate, slightly to moderately involute.

*Leaf division*.—Simple.

*Leaf base*.—Sheathing; 5.9 cm in length, 4.8 cm in width.

*Leaf apex*.—Narrow acuminate.

*Leaf venation*.—Parallel, upper surface a blend of NN137A and 147A, lower surface 147A.

*Leaf margins*.—Entire.

*Leaf attachment*.—Sessile, decurrent, no petioles.

*Leaf arrangement*.—Rosulate (rosette).

*Leaf orientation*.—Base held in an average angle of 40° to horizontal, tips arching downward in an average angle of 65° to leaf blade (varying 60° and 70°).

*Leaf surface*.—Both surfaces smooth and glabrous, upper surface glossy, lower surface moderately glossy.

*Leaf color*.—Young upper surface; 137A, young lower surface; 146A, tinged towards the base 175A, mature upper surface; a blend of NN137A and 147A, sheath N186C, base a blend of 152D and 160A, mature lower surface; 146A, sheath 152D, tinged with N186C, base 162B to 162C.

*Leaf size*.—Average of 17.9 cm in length and 2.1 cm in width.

*Leaf quantity*.—Average of 4 to 8 per rosette, 40 per plant.

Flower description:

*Inflorescence type*.—Terminal rhipidium with overlapping bracts, un-branched.

*Inflorescence size*.—An average of 10.6 cm in length and 4.1 cm in width (at widest part).

*Inflorescence position*.—Held completely above the foliage.

*Inflorescence quantity*.—2 to 8 per plant.

*Lastingness of flowers*.—Average of 5 days, persistent.

*Flower number*.—An average of 14 per inflorescence, 42 flowers and buds per plant.

*Flower size*.—Average of 1.3 cm in height and diameter, 5.2 cm in depth, throat; 2 mm in diameter, tube; 2.5 cm in length, 3 mm in diameter.

*Flower fragrance*.—None.

*Flower aspect*.—Outward to slightly upright.

*Flower type*.—Single, salverform.

*Flower bud*.—Lanceolate and triangular in shape, 3.8 cm in length, 6 mm in diameter, glabrous and slightly glossy surface, color; 154C and 154D, top 144C and 144B, base 37A to 37B.

*Petals*.—3, rotate, free portion narrow oblong, lower 62.5% of base fused, apex is obtuse with a minutely abrupt acute tip, margins entire and very slightly undulate, 4 cm in length, 3 mm in width, both surfaces smooth, glabrous, matte, color: when opening and fully open upper surface; 154D, top 151D, top 151A, when opening and fully open lower surface; 154D, top 151D, very tip 151B.

*Sepals*.—3, rotate in arrangement, average of 3 cm in length, 9 mm in width, linear and concave in shape, margins are entire, narrow acute apex, base broadly cuneate, both surfaces smooth, glabrous, and moderately glossy, color: when opening and fully upper surface; 160D, slightly tinged 35C at the base, when fully open upper and lower surface; 160D, slightly tinged 35B at the base.

*Calyx*.—Rotate, 3 cm in length, 6 mm in diameter.

*Peduncles*.—Average of 19.3 cm in length, 3 mm in diameter, held in an average of 50° to horizontal, strong, surface is glabrous and moderately glossy, 34B to 34D in color.

*Pedicels*.—None, individual flowers sessile.

*Bracts*.—Conduplicate bract covering each flower bud; ovate in shape, broadly acute apex, 4 cm in length, 2.3 cm in width (folded open), 1.2 cm in width (folded), color: inner surface 182D, outer surface; 45C, top N34A, bracts covering peduncle; ovate in shape, acuminate apex, 3.1 cm in length, 1.5 cm in width (folded open), 5 mm in width (folded), color: inner surface N34C, top 146A, outer tip 177A, outer surface; N34A, tinged at top 146A.

Reproductive organs:

*Gynoecium*.—Pistil; 1, average of 4.4 cm in length, style; 4.3 cm in length, 154C in color, stigma; flattened and club-shaped, 1 mm in length, 2 mm in diameter, 146C and 146D in color, ovary; 145A in color.

*Androecium*.—Stamens; 6, anthers; linear in shape, 5 mm in length, 1 mm in width, 197B in color, filament; 3.4 cm in length, color; 154C, pollen; abundant in quantity and 160° C. in color.

*Fruit/seeds*.—None observed to date.

It is claimed:

1. A new and distinct cultivar of *Vriesea* plant named 'Multred' as herein illustrated and described.

* * * * *